United States Patent [19]
Olney

[11] Patent Number: 5,616,580
[45] Date of Patent: Apr. 1, 1997

[54] PHARMACOLOGICAL COMPOSITION FOR PREVENTING NEUROTOXIC SIDE EFFECTS OF NMDA ANTAGONISTS

[76] Inventor: John W. Olney, #1 Lorenzo La., Ladue, Mo. 63124

[21] Appl. No.: 691,974

[22] Filed: Apr. 26, 1991

Related U.S. Application Data

[62] Division of Ser. No. 424,548, Oct. 20, 1989, Pat. No. 5,034,400.
[51] Int. Cl.$^6$ .......... A61K 31/54; A61K 31/445; A61K 31/135
[52] U.S. Cl. .......... 514/226.2; 514/315; 514/318; 514/646; 514/291
[58] Field of Search .......... 514/226.2, 315, 514/318, 646, 291

[56] References Cited

PUBLICATIONS

Olney et al. "Anti–parkinsonian agents are phencyclidine agonists and N–methyl–asparate antagonists." (1987).
Freedman et al, "Muscarinic $M_1$, $M_2$ receptor binding. Relationship with functional efficacy," (1988).

*Primary Examiner*—Marianne M. Cintins
*Assistant Examiner*—K. Weddington
*Attorney, Agent, or Firm*—Patrick D. Kelly

[57] ABSTRACT

This invention discloses mixtures of NMDA antagonists and anti-cholinergic agents, which can be used to prevent excitotoxic damage in the central nervous system or for anesthetic purposes in human or veterinary medicine. Anticholinergic agents such as scopolamine, atropine, benztropine, trihexyphenidyl, biperiden, procyclidine, benactyzine, or diphenhydramine can be used in conjunction with, or subsequent to, administration of an NMDA antagonist such as MK-801. The NMDA antagonist exerts a primary protective effect by preventing or reducing excitotoxic damage due to stroke, perinatal asphyxia, and various other types of injury or disease; however, strong NMDA antagonists such as MK-801 can also cause neurotoxic side effects, including vacuole formation, mitochondrial dissolution, and neuronal death in certain types of neurons such as cingulate/retrosplenial cerebrocortical neurons. The anti-cholinergic agent will reduce or eliminate those damaging side effects, without interfering with the primary protective value of the NMDA antagonist. The anti-cholinergic agents described herein can also reduce the toxic side effects associated with illegal use of drugs such as phencyclidine (also known as PCP or angel dust).

7 Claims, No Drawings

PHARMACOLOGICAL COMPOSITION FOR PREVENTING NEUROTOXIC SIDE EFFECTS OF NMDA ANTAGONISTS

This application is a divisional application of U.S. application Ser. No. 424,548, filed on Oct. 20, 1989, now Pat. No. 5,034,400.

BACKGROUND OF THE INVENTION

This invention is in the fields of pharmacology and neurology. It relates to compounds and methods for protecting the central nervous system against neurotoxic side effects of certain therapeutic drugs and against neurodegenerative disease processes.

Receptors, messenger molecules, agonists, and antagonists

The surfaces of nerve cells in the central nervous system (the CNS, which includes the brain, spinal cord, and retina) contain various types of receptor molecules. In general, a receptor molecule is a polypeptide which straddles a cell membrane. When a messenger molecule interacts with the exposed extracellular portion of the membrane receptor molecule, it triggers a difference in the electrochemical status of the intracellular portion of the receptor, which in turn provokes some response by the cell. The messenger molecule does not bond to the receptor; instead, it usually disengages from the receptor after a brief period and returns to the extracellular fluid. Most receptor molecules are named according to the messenger molecules which bind to them.

An "agonist" is any molecule, including the naturally occurring messenger molecule, which can temporarily bind to and activate a certain type of receptor. An agonist can cause the same effect as the natural messenger molecule, or in some cases it can cause a more intense effect (for example, if it has a tighter affinity for the receptor molecule and remains bound to the receptor for a prolonged period).

By contrast, an "antagonist" is a molecule which can block or reduce the effects exerted by the natural messenger molecule. This can happen in several different ways. A "competitive antagonist" binds to a certain type of receptor without triggering it, thereby preventing the natural messenger molecule from reaching and activating the receptor. A "non-competitive antagonist" functions in other ways. For example, a receptor referred to as the PCP receptor, which is triggered by molecules such as PCP or MK-801, apparently can override the effects of a different type of receptor, the NMDA receptor (both receptors are discussed below). Therefore, PCP and MK-801 are regarded as non-competitive antagonists for the NMDA receptor.

The role a certain molecule plays as an agonist or antagonist must be viewed with regard to a certain type of receptor. For example, while MK-801 is an antagonist for the NMDA receptor, it is an agonist for the PCP receptor. Most agonists and antagonists are xenobiotic drugs, i.e., they do not exist naturally in the body. For more information on neuroanatomy, neurotransmitters, receptors molecules, and agonists and antagonists which interact with CNS receptors, see Adelman 1987 (complete citations are provided below).

The two main classes of excitatory receptor molecules are referred to as "cholinergic" receptors and "glutamate" receptors. Both types of receptors are present in the synaptic junctions that serve as pathways for impulses between CNS nerve cells. Most other types of receptors in the CNS involve inhibitory neurotransmitters.

Excitatory amino acids and neurotoxicity

Accumulating evidence implicates excitatory amino acids (EAA's) such as glutamate and aspartate as causative agents in certain types of CNS damage associated with epsilepsy, hypoglycemia, hypoxia/ischemia (stroke, cardiac arrest, perinatal asphyxia), alcoholism, and trauma of the brain or spinal cord. It is also believed that EAA's may be involved in slowly developing neurodegenerative disorders such as Huntington's, Parkinson's and Alzheimer's diseases. Glutamate and aspartate (the ions or salts of glutamic acid and aspartic acid) are found naturally in high concentrations in the central nervous system (CNS) where they function as excitatory neurotransmitters.

Although these substances are beneficial and of critical importance for the normal functioning of the CNS, under abnormal conditions they can destroy CNS neurons by an "excitotoxic" process. Excitotoxicity refers to the process whereby EAA's that are released from one neuron excessively stimulate (excite) receptor molecules located on the external surface of another neuron. Excitotoxicity also refers to the same excitatory neurotoxic process when triggered by glutamate or EAA analogs of glutamate ingested in foods or administered systemically to various mammalian species. Glutamate and asparate are sometimes called "endogenous" excitotoxins, meaning that they are excitatory neurotoxins contained naturally within the CNS, whereas EAA ingested in foods or administered systemically are referred to as "exogenous" excitotoxins. For an extensive review, see Olney 1989.

EAA receptors, also known as glutamate receptors, are categorized into three subtypes, each named after a glutamate analog which selectively excites them: N-methyl-D-aspartate (NMDA), kainic acid (KA), and quisqualate (QUIS). Glutamate is capable of activating all three receptor subtypes.

Normally, relatively high glutamate concentrations (in the general range of about 10 mM) are maintained inside cells of the CNS, but high concentrations are not allowed in the extracellular fluid where glutamate can exert excitotoxic action at EAA receptors. After glutamate is released by a neuron for neurotransmitter purposes, it normally is transported back inside a cell by means of a transport mechanism which requires energy. Under severe low energy conditions such as hypoglycemia, hypoxia, or ischemia, the transport systems may lack sufficient energy to transfer extracellular glutamate back into the cell, so the glutamate accumulates at abnormal levels and excessively stimulates the EAA receptors. This can lead to continuous neuronal discharge, which in turn causes additional glutamate release and extracellular accumulation of excess glutamate, leading to a cascade of increasing neurotoxic injury, which can result in death or permanent damage to the brain.

Other mechanisms by which EAA's can cause neuronal injury include abnormal sensitivity of EAA receptors to the excitatory action of EAA's, and the presence of abnormal molecules (such as glutamate analogs, certain types of food poisons, etc.) with excitotoxic properties. Such receptor-triggering molecules can accumulate at EAA receptors because they are not recognized by the cellular transport systems as molecules which should be removed from the extracellular fluid.

In these neurotoxic situations, one method of preventing or minimizing excitotoxic injury to the neurons involves administering drugs that selectively block or antagonize the action of the excitotoxic molecules at the EAA receptors.

NMDA antagonists as neuroprotective drugs

The EAA receptor subtype that has been implicated most frequently in neurodegenerative diseases and neurotoxicity is the NMDA receptor. An entire issue of *Trends in Neurosciences* (Vol. 10, Issue 7, July 1987) was devoted to review articles pertaining to the NMDA receptor, and to NMDA "antagonists" (i.e., molecules which can block or reduce the effects of NMDA at NMDA receptors). Agents which act by binding directly to NMDA receptors, such as D-2-amino-5-phosphonopropanoate (D-AP5) and D-2-amino-7-phosphonoheptanoate (D-AP7), are referred to as competitive NMDA antagonists. Those two compounds are of limited therapeutic utility because they do not readily penetrate the blood-brain barrier. However, it is possible that some recently developed competitive NMDA antagonists, such as the Ciba-Geigy compound CGS 19755 (Boast, 1988) or 3-(2)-carboxypiperazin-4-yl)-propyl-1-phosphonate (CPP) or its unsaturated analog, CPP-ene, may affect the CNS following systemic administration (Herrling et al 1989).

The most powerful and effective NMDA antagonists known at the present time act at another receptor, the phencyclidine (PCP) receptor, which is considered a component of an ion channel complex that involves the NMDA receptor (Kemp et al 1987). These compounds are called non-competitive NMDA antagonists because they do not compete for binding sites at NMDA receptors. When phencyclidine or its analogs activate the PCP receptor, the flow of ions through the NMDA ion channel is blocked or substantially reduced, so that when the NMDA receptor is activated by an EAA, the NMDA receptor response does not result in the flow of ion currents. This blocks the excitation of the neuron.

Four compounds which can activate the PCP receptor, and which therefore serve as non-competitive NMDA antagonists, are phencyclidine, MK-801, ketamine, and tiletamine. Each is discussed in more detail below. All four of these agents can penetrate the blood-brain barrier.

MK-801, a phencyclidine analog manufactured by Merck, Sharp and Dohme (Rahway, N.J.) is believed to be the most powerful PCP agonist of the four compounds listed above (Olney et al 1987). It has generated great interest recently, largely due to its potential for reducing neurotoxic damage involving NMDA receptors. The chemical name for MK-801 is (+)-5-methyl-10,11-dihydro-5H-dibenzo[a,d]cyclohepten-5,10-imine maleate.

Neurological problems that might be aided by NMDA antagonists

Non-competitive NMDA antagonists have been shown in in vivo animal experiments (reviewed in Olney 1989) to protect CNS neurons against damage caused by persistent seizures, hypoglycemia, hypoxia/ischemia, trauma, thiamine deficiency, and methamphetamine poisoning (a form of neurotoxicity related to Parkinson's disease). It is possible, therefore, that such agents might be used therapeutically for neuroprotective purposes in conditions such as the above.

It is also possible that NMDA antagonists might be used to prevent brain damage associated with alcoholism. In chronic alcoholics, neuronal degeneration has been described in several regions of the brain, including periventricular and periaqueductal regions, the thalamus, the hypothalamus, and mammillary bodies. Individuals with this type of brain damage manifest a form of dementia known as Wernicke/Korsakoff syndrome, which includes severe deficits in memory and cognitive functions. It is believed that this syndrome relates to dietary deficiencies, especially thiamine (vitamin B) deficiency. It is known that people who suffer from thiamine deficiency are subject to the same pattern of brain damage and the same dementing Wernicke/Korsakoff syndrome that is seen in alcoholism. Recently, it was demonstrated that in a rat model of thiamine deficiency, which entails disseminated brain damage distributed in a Wernicke/Korsakoff pattern, the brain damage can be markedly attenuated by pretreatment with MK-801 (Langlais et al 1988). That result suggests that this type of brain damage is mediated by an excitotoxic mechanism involving the NMDA receptor ion channel complex, and that patients with acute symptoms suggesting an impending Wernicke/Korsakoff syndrome might benefit from treatment with an NMDA antagonist such as MK-801.

It is also suspected that there may be a link between virally-induced neurodegenerative conditions and NMDA receptor-mediated excitotoxicity (Olney 1989). When a viral infection triggers changes in neural homeostasis, endogenous excitotoxins such as glutamate and aspartate may become involved in cell death or damage. Therefore, NMDA antagonists such as MK-801 may be useful for preventing neuronal degeneration associated with viral infections that involve the CNS, such as Jacob-Creutzfeldt syndrome and encephalitis associated with herpes or measles infection.

NMDA antagonists such as MK-801 might also be useful for protecting against brain damage associated with a newly recognized type of food poisoning. In January 1988, there was an outbreak of food poisoning in Canada affecting 145 identified individuals, some of whom died and were found at autopsy to have widespread brain damage (Quilliam et al 1989). Some of the surviving victims suffered severe brain damage and became permanently demented. All of the victims had ingested mussels from the Newfoundland region. Analysis of the mussels revealed a high concentration of domoate, a powerful convulsant which apparently causes brain damage by inducing persistent seizure activity which releases excessive glutamate, triggering an excitotoxic cascade. It is believed that domoate poisoning may become a recurrent problem in several regions of the world. The inventor of the subject invention has recently demonstrated that certain NMDA antagonists (including MK-801 and phencyclidine) protect against domoate neurotoxicity. Therefore, NMDA antagonists such as MK-801 may serve as antidotes to prevent brain damage, dementia and/or death in domoate poisoning.

In addition to seizure-related brain damage associated with domoate poisoning, brain damage also occurs as a result of persistent seizures in patients with epilepsy. In this situation also, it is believed that excessive activation of NMDA receptors by endogenous glutamate may cause or exacerbate brain damage. It is possible, therefore, that patients who come to emergency rooms in status epilepticus (a state of continuous epileptic seizure activity) might be protected from permanent brain damage by timely treatment with an NMDA antagonist.

However, the potential therapeutic uses of MK-801 and other NMDA antagonists must be viewed with caution, because it has recently been discovered (Olney et al 1989) that such agents can inflict their own type of neurological damage.

The subject invention, as explained below, involves a class of protective agents that can be administered along with NMDA antagonists such as MK-801, to reduce or eliminate the dangers and deleterious side effects of NMDA antagonists. The subject invention thereby enables the safe use of NMDA antagonists such as MK-801 to accomplish the beneficial results set forth above.

Neurotoxic side effects of NMDA antagonists

A potentially serious side effect of MK-801, phencyclidine, and related drugs is that they may induce a neurodegenerative reaction in the posterior cingulate and retrosplenial cerebral cortex, even when administered in relatively low doses (Olney et al 1989). In a series of experiments, MK-801 and phencyclidine were given to adult rats to test for neuroprotection against seizure-related brain damage. Those agents did protect neurons in certain brain regions from seizure-related damage, but they also caused a different type of neurotoxic reaction in other brain regions, the posterior cingulate and retrosplenial cerebral cortices. The neurotoxic reaction, which was observed during microscopic analysis of CNS tissue after the rats were sacrificed, consisted of the formation of vacuoles (membrane-enclosed spaces in the cytoplasm that are not present in normal cells) and the dissolution of mitochondria (energy-producing organelles inside the cells). Although these changes appeared to be reversible if the doses of MK-801 or phencyclidine were sufficiently low, it has recently been discovered that irreversible necrosis of cingulate cortical neurons follows the administration of 5 mg/kg MK-801.

In adult rats, the $ED_{50}$ for producing vacuoles in cingulate neurons by MK-801 administration (i.e., the dosage of MK-801 which will produce vacuoles in 50% of the animals treated) is 0.18 mg/kg, administered intraperitoneally (ip; Olney et al 1989). Since the doses of MK-801 used in animal experiments for protecting neurons against ischemic brain damage usually are in the range of 1 to 10 mg/kg, it appears that the use of MK-801 for therapeutic neuroprotection poses a major risk of inducing potentially serious neurotoxic side effects.

The mechanism by which MK-801, phencyclidine and related drugs cause vacuole formation in cingulate/retrosplenial neurons is poorly understood. However, recent evidence that this effect can be reproduced by microinjection of a competitive NMDA antagonist (D-AP5) into the cingulate cortical region (Labruyere et al 1989) suggests that any agent that antagonizes the NMDA receptor ion channel complex by any mechanism may have this toxic property, since the vacuole reaction occurs when NMDA receptor function is suppressed, either by direct antagonist binding of D-AP5 to the NMDA receptor, or by interaction of MK-801 at the level of the NMDA receptor ion channel. An important implication of this finding is that some recently developed competitive NMDA antagonists which may be able to penetrate the brain in sufficient concentration to be used as neuroprotective drugs, such as CGS 19755, CPP, and CPP-ene, may not provide an acceptable alternative to the non-competitive NMDA antagonists, since both groups of compounds might cause the same type of neurotoxic side effect. These findings and implications suggest that both groups of compounds would be more acceptable for therapeutic purposes if a method were found that prevents their neurotoxic side effects without interfering with their neuroprotective actions.

History of the uses and abuses of NMDA antagonists

Phencyclidine (PCP) was originally introduced into clinical medicine some 30 years ago as an anesthetic (Goodman and Gilman 1975). Shortly thereafter, it was withdrawn from the market because it was found to have hallucinogenic properties which invited illicit use by drug abusers. Since then, PCP (also known as angel dust) has become increasingly popular as a "recreational" drug and currently is a major cause of drug-induced psychotic reactions (which occasionally lead to extremely violent crimes) among drug abusers. The pathomorphological effect of PCP (vacuole formation and mitochondrial dissolution in certain types of neurons) might be related to the mechanism by which PCP causes toxic psychoses. Thus, if a drug could be found that prevents the pathomorphological effects of PCP, it might also prevent or ameliorate the psychotomimetic effects of PCP. Such a drug might be used in emergency rooms, or perhaps by the police, as an antidote to reduce both the neurological damage and the psychotic effects of PCP in drug abusers.

Ketamine, a drug manufactured by Parke Davis and marketed under the trade name Ketalar, is currently used both in human and in veterinary medicine as an anesthetic. Ketamine is known to activate PCP receptors and, like PCP and MK-801, is recognized as a non-competitive antagonist of the NMDA receptor-ion channel complex (Kemp et al 1987). Ketamine was among the drugs recently shown to produce pathomorphological effects on cingulate/retrosplenial neurons following intraperitoneal (ip) administration to rats (Olney et al 1989). Ketamine is known to induce an acute transient psychosis (called an "emergence" reaction) in about 13% of human patients anesthetized with this agent (Physicians Desk Reference, 1986). It has been proposed that the psychotic effects of ketamine, like those of PCP, may be psychological manifestations of the same toxic process that causes pathomorphological changes in cingulate/retrosplenial neurons, in which case a drug that could prevent the pathomorphological changes might also prevent or reduce the psychotic manifestations. Even without preventing the psychotic manifestations, eliminating the risk of pathomorphological changes would be a significant benefit.

Tiletamine is a drug manufactured by A. H. Robins. It is currently used in veterinary medicine, and is widely used for anesthesia on house pets. Tiletamine, like PCP, MK-801 and ketamine, is known to activate PCP receptors and is recognized as a non-competitive antagonist of the NMDA receptor-ion channel complex. Tiletamine was among the drugs recently shown to produce pathomorphological effects on cingulate/retrosplenial cortical neurons following ip administration to rats (Olney et al 1989).

MK-801, a drug manufactured by Merck, Sharp and Dohme and referred to as dizocilpine, was initially proposed as an anticonvulsant, but after brief human clinical trials, it was withdrawn from further testing several years ago with no published explanation. At about the same time, it was discovered that MK-801 is a potent activator of PCP receptors (with higher affinity for the PCP binding site than PCP itself; MK-801 is more specific for PCP receptors than any other known compound), and that PCP receptors are an integral component of the NMDA receptor ion channel complex (Kemp et al 1987). It was also found that both MK-801 and PCP block the excitatory effects of NMDA on neurons in the in vivo rat spinal cord (Lodge et al 1987). In neurotoxicology studies, using an ex vivo chick embryo retina assay, it was shown that MK-801 is approximately 5–10 times more powerful than PCP in preventing the neurotoxic effects of NMDA on retinal neurons (Olney et al 1987). Previously, PCP had been recognized as the most powerful known antagonist of NMDA neurotoxicity (Olney et al 1986).

Because of its great potency and the ease with which it penetrates blood brain barriers, MK-801 has become the drug used most widely in animal experiments aimed at testing the neuroprotective properties of NMDA antagonists. Since it has now been shown to protect CNS neurons against various degenerative processes that are thought to involve excessive activation of NMDA receptors (e.g., hypoxia/ ischemia, prolonged seizures, hypoglycemia, thiamine deficiency, head or spinal cord trauma) there is considerable interest in using MK-801 for neuroprotective purposes in clinical neurology. Clearly, it would be desirable to have a means of preventing the toxic action of MK-801 on cingulate/retrosplenial cortical neurons, thereby making this drug available for human therapy with reduced risk of neurotoxic side effects.

Cholinergic receptors

Cholinergic receptors are activated by acetylcholine, a relatively small molecule released by certain types of brain cells. Cholinergic receptors are divided into two main classes: muscarinic and nicotinic.

Little is known about nicotinic receptors in the CNS. They exist in the peripheral nervous system, at neuromuscular junctions, and they are presumed to exist inside the brain, but very limited progress has been made in developing agonist or antagonist molecules that can penetrate blood-brain barriers and be used to pharmacologically characterize nicotinic receptors that may exist in the brain.

Muscarinic receptors are subdivided into M1 and M2 receptors, based on the discovery that pirenzepine binds with much greater affinity to one subpopulation (M1) found primarily in the forebrain, than to a separate subpopulation (M2) that exists primarily in the hindbrain and in the peripheral nervous system. Most anti-cholinergic molecules, although more powerful than pirenzepine in binding to cholinergic receptors, do not show as high a degree of specificity for one receptor subpopulation. Thus, the anti-cholinergic agents of primary interest herein have substantial affinity for both M1 and M2 receptors (Burke 1986; Freedman et al 1988). It is not known whether or to what extent these anti-cholinergics also interact with nicotinic receptors inside the brain, since reliable methods for identifying and characterizing nicotinic receptors in the brain have not been available.

Pilocarpine, a cholinergic agonist used in epilepsy research, has been shown to cause seizures and seizure-related brain damage (Turski et al 1983; Clifford et al 1987). Although the inventor has used MK-801 successfully to prevent brain damage associated with seizures induced by various methods, a set of experiments described in Example 5 indicates that MK-801 has a potentiating effect when administered along with pilocarpine. The term "potentiate" refers to the fact that the MK-801 lowered the seizure threshold and made test animals susceptible to seizures at a pilocarpine dosage that would not have caused seizures in the absence of the MK-801. This finding raises questions about whether NMDA antagonists would tend to induce seizures in humans who suffer from epilepsy.

The inventor also discovered that pilocarpine and MK-801, when administered together, increase the formation of vacuoles in cingulate/retrosplenial neurons. If an adult rat is treated with pilocarpine (75 mg/kg ip), the $ED_{50}$ of MK-801 for producing cingulate/retrosplenial vacuoles is reduced from 0.18 mg/kg to 0.05 mg/kg.

Judging from these results, MK-801 apparently can exert one type of beneficial anti-convulsant effect, by blocking one of the major excitatory transmitter systems, the NMDA receptor system. However, MK-801 appears to potentiate another type of seizure activity mediated by the cholinergic receptor system. These results imply that some kind of mechanism exists by which the cholinergic and NMDA receptor systems are linked, such that drugs affecting either system can influence neurological disorders such as seizure activity and formation of vacuoles in cingulate/retrosplenial neurons.

Anti-cholinergic agents

A group of agents classified as anti-cholinergics (i.e., they block the activation of cholinergic receptors) have been used in clinical neurology as anti-parkinsonian drugs (Goodman and Gilman 1975). These agents were recently found by the inventor to protect rats against the convulsant and brain damaging action of pilocarpine and another cholinergic neurotoxin, soman (Price et al 1989). The drugs that conferred this neuroprotective action are procyclidine, biperiden and trihexyphenidyl, which are structurally related compounds of the aryl-cyclo-alkanolamine class. These agents, especially biperiden and trihexyphenidyl, are considered cholinergic antagonists that act quite powerfully at the M1 muscarinic receptor (Freedman et al 1988), which suggests a possible explanation for their efficacy in blocking the neurotoxic actions of pilocarpine, which is primarily an M1 cholinergic agonist. These aryl-cycloalkanolamines have also been shown to have limited effectiveness as NMDA receptor antagonists (Olney et al 1987), but they are considered much more powerful as M1 cholinergic antagonists than as NMDA antagonists.

Procyclidine, which has some degree of affinity for NMDA receptors in addition to being an anti-cholinergic agent, can be administered to adult rats at a high dose (75 mg/kg) without producing neurotoxic side effects such as cingulate/retrosplenial vacuole formation induced by other NMDA antagonists such as MK-801 or D-AP5. Procyclidine is described in U.S. Pat. No. 2,891,890 (Adamson 1959), and is marketed under the trade name "Kemadrin" by Burroughs-Wellcome.

Biperiden has been studied for its mood altering effects (Fleischhacker et al 1987) and for its interaction with muscarinic receptors (Syvalahti et al 1987). The hydrochloride salt of biperiden has been studied for its interaction with nicotine and oxotremorine in rat diaphragm (Das et al 1977). Biperiden is marketed under the trade name "Akineton" by Knoll. Triperiden is marketed in Europe under the trade name "Norakin" by VEB Fahlberg-List (Magdeburg, West Germany).

Trihexyphenidyl has been studied for its effects in schizophrenic patients (Hitri et al 1987) and for its effects on memory in elderly patients (McEvoy et al 1987). It is marketed under the trade name "Artane" by Lederle, and is used to reduce Parkinson symptoms in schizophrenics who are being treated with phenothiazine compounds.

Various other aryl-cycloalkyl-alkanolamine compounds have also been studied for varying purposes (e.g., U.S. Pat. Nos. 4,031,245 and 3,553,225, West German Offen. No. 1,951,614, and Mann et al 1976). However, none of the research with this class of compounds involves their use for reducing the neurotoxic effects of PCP, MK-801, or other NMDA antagonists.

A number of other compounds are known to function as anti-cholinergic agents. Benztropine, sold under the trade name "Cogentin" by Merck, Sharp and Dohme, is used to reduce Parkinson symptoms in schizophrenics being treated with phenothiazine compounds (Vernier 1981). Benactyzine is used in conjunction with meprobamate in a formulation called "Deprol," sold by Wallace Laboratories (Physicians Desk Reference 1989, p. 2200). Scopolamine and atropine, both of which have been used widely in medicine for anesthesia-related purposes, have also been used as anti-Parkinsonian drugs, but they tend to cause side effects when administered at anti-Parkinson dosages, due to their interactions with cholinergic receptors in the peripheral nervous system. In summary, accumulating evidence suggests that NMDA antagonists might be highly useful therapeutic agents in various neurological disorders. However, prior to this invention, there was no known agent or method for preventing certain deleterious side effects of those NMDA antagonists.

One object of this invention is to provide a pharmacological agent and method which can be used in human medicine to reduce the neurotoxicity of NMDA antagonists.

Another object of this invention is to provide an agent and a method for reducing the neurotoxicity of agents such as ketamine and tiletamine, which are used as veterinary anesthetics on animals including house pets.

Another object of this invention is to provide a mixture of an NMDA antagonist combined with a protective agent which reduces the neurotoxic effects of the NMDA antagonist. Such mixtures can be used to prevent or minimize deleterious CNS effects associated with various neurological disease processes.

SUMMARY OF THE INVENTION

This invention involves drugs that can be used to reduce the neurotoxic side effects that can be caused when NMDA antagonists are used as anti-convulsants, to prevent excitotoxic damage in the central nervous system, or for anesthetic purposes in human or veterinary medicine. This method involves the use of anti-cholinergic agents such as scopolamine, atropine, benztropine, trihexyphenidyl, biperiden, procyclidine, benactyzine, or diphenhydramine in conjunction with, or subsequent to, administration of an NMDA antagonist such as MK-801. The anti-cholinergic agents greatly reduce or eliminate the deleterious side effects that can accompany NMDA antagonists (such as convulsion potentiating effects, as well as vacuole formation, mitochondrial dissolution, and possible death of cingulate/retrosplenial cerebrocortical neurons), without interfering with the useful properties of the NMDA antagonists. The protective agents described herein may also reduce the neurotoxic, psychotoxic, and/or hallucinatory side effects associated with illegal use of drugs such as phencyclidine. Mixtures of NMDA antagonists and anti-cholinergic agents as disclosed herein can be used for beneficial purposes, such as providing safe anesthesia or ameliorating neurological disease processes, while also preventing deleterious side effects that might otherwise be caused by the NMDA antagonists.

DESCRIPTION OF THE PREFERRED EMBODIMENTS

This invention relates to a class of protective compounds that can reduce the neurotoxic effects of NMDA antagonists. These protective compounds are classified as anti-cholinergic agents, since they block the triggering effects of acetylcholine molecules at cholinergic receptors. Prior to this invention, it was not realized that anti-cholinergic agents could prevent neurotoxic effects caused by agents which affect glutamate receptors, an entirely different class of receptors.

As used herein, the terms "neurotoxic effects" and "deleterious neurological effects" caused by NMDA antagonists refer to any of the following: (1) the formation of observable vacuoles in any type of CNS cell, if comparable vacuoles of similar number, size, or type are not detected in neurons of the same type in healthy, untreated animals; (2) the causation of damage to, dissolution of, or other significant alterations in substantial numbers of mitochondria in CNS cells; (3) the death of, or necrotic signs in, significant numbers of cerebrocortical neurons if attributable to administration of an NMDA antagonist; (4) the generation of psychotoxic or hallucinatory effects, such as the psychotomimetic effects of PCP, or the "emergence reaction" suffered by some patients who are anesthetized by ketamine; or, (5) convulsion potentiating effects.

The anti-cholinergic agents which have been tested thus far to determine whether they can prevent neuronal vacuole formation caused by NMDA antagonists such as MK-801 and PCP include the following compounds, which are listed in decreasing order of potency, measured by their ability to prevent vacuole formation by MK-801 administered at 0.4 mg/kg (i.e., 0.4 milligrams of MK-801 per kilogram of animal body weight, as described in Example 1):

1. Scopolamine provides the highest degree of protection discovered to date. It was completely effective on all animals tested to date at 0.25 mg/kg.

2. Benztropine provided complete protection for all animals tested to date at 2 mg/kg.

3. Trihexyphenidyl and atropine protected all animals tested to date when administered at 5 mg/kg.

4. Biperiden, procyclidine, and benactyzine protected all animals at 10 mg/kg.

5. Diphenhydramine, which is usually classed as an H1 histamine antagonist but which also has anti-cholinergic activity, protected all animals at 25 mg/kg.

Additional information is contained in Table 1. The test data are based on limited numbers of tests done to date, using the procedures described in the Examples. As will be recognized by those skilled in the art, these data will need to be confirmed and carefully evaluated by more extensive testing; however, the results obtained thus far are quite clear and highly significant.

A second key finding is that the anti-cholinergic agents listed above and in Table 1, at doses insufficient to totally prevent vacuole formation, substantially decreased both the number and the size of the cingulate/retrosplenial vacuoles that were caused by the MK-801. This result is not reflected in the tables, which indicate only the presence or absence of any detectable vacuoles. Clearly, a substantial reduction in the number and/or the size of vacuoles indicates that the neurotoxic properties or activities that are manifested by vacuole formation are being mitigated by the anti-cholinergic agents.

Some anti-cholinergic agents (such as dicyclomine and pirenzepine) may be of limited value for protecting against NMDA antagonist neurotoxicity, since they bind only weakly to cholinergic receptors in the brain. It should be noted that dicyclomine and pirenzepine are often referred to in the literature as "highly selective" M1 antagonists. This can be confusing, since their affinity for M1 receptors is relatively weak compared to other M1 antagonists such as scopolamine. The "highly selective" M1 attribute derives from the fact that they have extremely weak affinity for M2 receptors, as indicated in Table 2, which is derived from Freedman 1988 at page 136. The $K_{app}$ values provided by Freedman et al are, in effect, dissociation values; a high $K_{app}$ value indicates weak binding. Therefore, the value $1/K_{app}$ provides an indicator of affinity. As can be seen from Table 2, although dicyclomine and pirenzpine have high M1/M2 ratios, their affinity for M1 receptors is only a small fraction of the affinity of other compounds such as scopolamine.

In addition, preliminary experiments indicate that N-methylscopolamine is of virtually no value for use as described herein, even though it is a potent anti-cholinergic agent. This was expected, since methylscopolamine does not penetrate the blood-brain barrier in substantial quantities.

The data in Tables 1 and 2 suggest that the blocking of M1 receptors is heavily involved in the neuroprotective action of anti-cholinergic agents. This follows from the data indicating that atropine offered a lower degree of protection than scopolamine. However, all of the anti-cholinergics tested to date have a substantial degree of affinity for both M1 and M2 receptors.

As mentioned previously, it is not known whether or to what extent any anti-cholinergic agents bind to nicotinic receptors inside the CNS, because of the lack of appropriate methods for studying nicotinic receptors within the CNS. As the state of knowledge regarding nicotinic receptors advances, any anti-cholinergic agents which pass through the blood-brain barrier and which are reliably identified as antagonists of CNS nicotinic receptors can be screened for protective activity against the neurotoxic effects of NMDA antagonists such as MK-801, using the procedures described herein. Despite the current limited knowledge regarding nicotinic receptors, every anti-cholinergic agent tested to date which can penetrate the blood-brain barrier has been demonstrated to be effective in reducing the neurotoxic side effects of MK-801.

One of the anti-cholinergic compounds (biperiden) has also been shown to be effective in preventing vacuole formation by phencyclidine (PCP), as described in Example 3. Since PCP and MK-801 both bind to and activate PCP receptors in the CNS, it is believed that any anti-cholinergic compounds which provide effective protection against the side effects of MK-801 will also protect against PCP neurotoxicity, and therefore could be used to counteract the permanent damage and possibly the psychotic symptoms of PCP ("angel dust") when abused by illegal users. The anti-cholinergic compounds discussed herein have also been tested to ensure that they do not interfere with the desirable neuroprotective properties of MK-801, an agent that shows great promise in blocking excitotoxic damage involving glutamate receptors. As described in Example 4, the results are quite favorable; the anti-cholinergic agents tested to date apparently do not interfere with the beneficial effects of MK-801.

Another set of experiments, described in Example 5, indicate that NMDA antagonists may have convulsion-potentiating effects when cholinergic receptors are being excessively stimulated. The NMDA antagonist used (MK-801) lowered the seizure threshold and made animals more susceptible to seizures, when the animals were treated with a cholinergic agonist (pilocarpine) at a dosage that would not have caused seizures in the absence of the NMDA antagonist. This finding raises questions about whether NMDA antagonists would also tend to induce seizures in humans who suffer from epilepsy. However, it was also discovered that the administration of biperiden, an anti-cholinergic, along with MK-801 and pilocarpine, protected the animals against any seizure activity, brain damage, and vacuole formation in cerebrocortical neurons. This result indicates that the vacuole-inducing properties and the convulsion potentiating properties of an NMDA antagonist such as MK-801 can be prevented by an anti-cholinergic agent.

A preferred embodiment of the subject invention comprises a mixture of (1) an NMDA antagonist such as MK-801, and (2) an anti-cholinergic protective agent. The NMDA antagonist can be used for beneficial purposes such as human or veterinary anesthesia or to protect against excitotoxic or neurodegenerative processes associated with various conditions described above. The anti-cholinergic agent will prevent or minimize deleterious side effects (such as convulsions, hallucinations, or pathological changes or necrosis of cerebrocortical neurons) that might otherwise be caused by the NMDA antagonist. By reducing the deleterious side effects of the NMDA antagonist without interfering with its useful activity, the anti-cholinergic agent can render the mixture a more safe and effective formulation. Included within the family of anti-cholinergic agents useful for the purposes described herein are any tautomeric or isomeric forms or analogs which function as cholinergic antagonists (i.e., which block the activation of cholinergic receptors by endogenous acetylcholine molecules). The anti-cholinergic activity of any such tautomer, isomer, or analog can be tested using various methods known to those skilled in the art, such as competitive binding assays using radioactive isotopes of prototypic cholinergic agonists or antagonists, as described in, e.g., Freedman et al 1988 or Burke 1986.

Also included within the compounds of this invention are pharmaceutically acceptable salts of anti-cholinergic agents. The term "pharmaceutically-acceptable salts" embraces salts commonly used to form alkali metal salts and to form addition salts of free acids or free bases. The nature of the salt is not critical, provided that it is non-toxic and does not substantially interfere with the anti-cholinergic activity. Examples of acids which may be employed to form pharmaceutically acceptable acid addition salts include inorganic acids such as hydrochloric acid, sulphuric acid and phosphoric acid, and organic acids such as maleic acid, succinic acid and citric acid. Other salts include salts with alkali metals or alkaline earth metals, such as sodium, potassium, calcium and magnesium. All of these salts may be prepared by conventional means.

For the purposes of this invention, it does not matter whether an anti-cholinergic agent has any other pharmaceutical effect, so long as it is capable of blocking at least one type of cholinergic receptor. For example, diphenhydramine is an anti-cholinergic agent even though it also has the characteristic of being an anti-histamine. Similarly, a compound is regarded as an anti-cholinergic agent if it blocks at least one type of cholinergic receptor, regardless of whether it also blocks other types of cholinergic receptors.

The anti-cholinergic compounds tested to date are all commercially available; in addition, methods of synthesis of these compounds are known to those skilled in the art. For example, synthesis of procyclidine and its salts are shown in U.S. Pat. Nos. 2,891,890 and 2,826,590. Synthesis of trihexyphenidyl hydrochloride is described in U.S. Pat. No. 2,682,543. Synthesis of biperiden is described in U.S. Pat. No. 2,789,110.

Administration of anti-cholinergic compounds to humans can be by any technique capable of introducing the compounds into the bloodstream of a human patient, including oral administration or intravenous, intramuscular and subcutaneous injections. The active compound is usually administered in a pharmaceutical formulation such as in a liquid carrier for injection, or in capsule form for ingestion, although in some acute-care situations an anti-cholinergic agent might be injected without a diluting agent. Such formulations may comprise the active compound (or a mixture of more than one anti-cholinergic compounds) together with one or more pharmaceutically acceptable carriers or diluents. Other therapeutic agents may also be present in the formulation. Delivery of the active compound in such formulations may be by various routes including oral, nasal, topical, buccal and sublingual, or by parenteral administration such as subcutaneous, intramuscular, intravenous, or intradermal routes.

EXAMPLES

EXAMPLE 1: TESTING ANTI-CHOLINERGICS AT VARYING DOSAGES

Adult female Sprague Dawley rats, approximately 4 months old, were used in these experiments. It was previously established (Olney et al 1989) that the $ED_{50}$ for producing vacuoles in female Sprague Dawley rats is 0.18 mg/kg of MK-801 when administered subcutaneously (sc). In those earlier experiments, MK-801 produced the vacuole effect in 75% of the animals at 0.2 mg/kg sc, and in 100% at doses of 0.3 and 0.4 mg/kg sc. In the present experiment, MK-801 was administered at a dose of 0.4 mg/kg sc, a dosage more than high enough to produce vacuoles in all animals.

Ten minutes after the MK-801 was administered, the rats received an intraperitoneal (ip) injection of scopolamine, benztropine, trihexyphenidyl, atropine, biperiden, procyclidine, benactyzine, or diphenhydramine, at a range of different doses shown in Table 1. Four animals were used in each treatment group, with a concurrent control group (MK-801 alone) for each test compound.

It was previously established (Olney et al 1989) that the vacuole effect becomes clearly observable within 4 hours following MK-801 treatment. Therefore, the rats were anesthetized and sacrificed by perfusion fixation of the CNS at 4 hours following MK-801 treatment, using a mixture of glutaraldehyde and paraformaldehyde injected into the left cardiac ventricle. Their brains were processed by methods permitting histopathological evaluation by both light and electron microscopy, as described in Olney 1971. The tissue samples were evaluated using numerical codes, by an experienced histopathologist who had no knowledge of the treatment conditions for any given tissue sample.

In all control rats (32 of 32), a severe vacuole reaction in cingulate/retrosplenial cerebrocortical neurons was observed. As indicated in Table 1, all of the anti-cholinergic agents prevented vacuole formation in a dose-related manner. All except diphenhydramine provided total protection at doses above 5 mg/kg, and atropine, trihexyphenidyl, benztropine, and scopolamine gave complete protection at doses above 2, 2, 1, and 0.1 mg/kg, respectively. When vacuoles were present in rats treated with doses below the thresholds for complete protection, the number and size of the vacuoles usually appeared smaller than in the control rats. Thus, the degree of protection conferred is conservatively stated when described in terms of the number of brains with vacuoles.

EXAMPLE 2: TESTING MK-801 AT VARYING DOSAGES

The lowest dose of biperiden (10 mg/kg) that provided complete protection against MK-801 vacuole formation in Example 1 was administered to rats that received MK-801 on an increasing dose schedule (1, 2.5 and 5 mg/kg). It was found that the same low dose of biperiden (10 mg/kg) that had protected against 0.4 mg/kg MK-801 in Example #1 also protected completely against doses of MK-801 up to and including 5 mg/kg. In all experiments, the biperiden was well-tolerated by the rats. The *Physicians Desk Reference* indicates that the $LD_{50}$ for biperiden in adult rats is 270 mg/kg, so the margin of safety between effective and toxic doses is quite favorable.

EXAMPLE 3: PCP TESTING

In order to determine whether anti-cholinergic agents protect against the vacuole-forming neurotoxicity of NMDA antagonists other than MK-801, female adult Sprague Dawley rats were treated with PCP (10 mg/kg sc). Ten minutes later, they were treated with biperiden at doses of 10, 5, and 1 mg/kg ip. A dose-related protective effect was demonstrated. PCP caused a severe vacuole reaction in all control rats (4/4), and in 0/4, ¾, and ¼ rats treated with biperiden at 10, 5, and 1 mg/kg respectively.

EXAMPLE 4: NON-INTERFERENCE WITH DESIRED MK-801 EFFECTS, USING NMDA AT EXCITOTOXIC LEVELS

To determine whether anti-cholinergics interfere with the ability of MK-801 to protect neurons against the excitotoxic action of NMDA, an ex vivo chick embryo retina assay was used. This preparation has been found useful for studying the excitotoxic effects of NMDA on CNS neurons and for evaluating the ability of antagonists to protect against NMDA excitotoxicity (Olney 1989). In these experiments, 18 segments of chick retina were incubated, each in a separate well, in medium containing NMDA at a concentration of 80 micromolar (uM), which previously had been determined to produce a fully developed excitotoxic lesion in 30 minutes. MK-801 was added to 12 wells at 0.2 uM, a threshold concentration known to consistently block the neurotoxic action of NMDA; in 6 of those wells, both MK-801 (0.2 uM) and biperiden (50 uM) were added.

In the six wells containing NMDA but no MK-801, a full retinal lesion was present within 30 minutes. In all twelve wells that contained both NMDA and MK-801, the MK-801 blocked the neurotoxic action of the NMDA, either in the presence of biperiden (6/6) or in absence of biperiden (6/6). Therefore, even when biperiden was present in CNS tissue at a concentration 250 times higher than the concentration of MK-801, it did not prevent the MK-801 from exerting its neuroprotective action against the excitotoxic processes mediated by NMDA triggering of NMDA receptors.

In Example 2, it required a dose of only 10 mg/kg biperiden to completely block the neurotoxic effects of 5 mg/kg MK-801 on cingulate/retrosplenial cortical neurons. Thus, when BPN and MK-801 are present in a 2:1 ratio, biperiden protects against MK-801's neurotoxic side effects, but when present in a 250:1 ratio, biperiden does not interfere with MK-801's ability to potect against NMDA receptor-mediated neurodegenerative processes.

EXAMPLE 5: DEMONSTRATION OF THE CONVULSION POTENTIATING EFFECTS OF MK-801, AND PROTECTION USING BIPERIDEN

Pilocarpine is a cholinergic agonist which causes seizures and seizure-related brain damage. It is used in research pertaining to epilepsy, since it is believed that the receptor mediated processes involved in pilocarpine-induced seizures are similar in some respects to the mechanisms of epileptic seizures. Although the pilocarpine dosage that induces seizures and seizure-related brain damage varies between individual rats, it is usually in the range of about 380–400 mg/kg sc.

The Applicant previously established that MK-801 can reduce or eliminate seizures and seizure-related brain damage caused by various methods (Clifford et al 1989). However, when the inventor tried to use MK-801 to reduce seizures induced by pilocarpine, he discovered that the combination of MK-801 and pilocarpine resulted in a severe seizure-brain damage syndrome at relatively low doses (50 mg/kg sc pilocarpine, injected 10 minutes after 1 mg/kg sc MK-801). At those doses, neither agent by itself can cause seizures or seizure-related brain damage. The MK-801 therefore potentiates the effects of pilocarpine, i.e., it lowers the seizure threshold and makes the animal more susceptible to a seizure. These observations—that MK-801 protects against some types of seizure-brain damage syndrome but potentiates other such syndromes—suggest that MK-801 might have unpredictable and in some cases adverse effects in humans who are subject to epileptic seizures, and in humans who are being treated with various neuropharmacological drugs.

Adult rats were also treated with both MK-801 (1 mg/kg sc) and biperiden (10 mg/kg ip); ten minutes later, they were injected with pilocarpine (50 mg/kg sc). The additional presence of the biperiden prevented all neurotoxic manifestations, including seizure activity, the widespread brain damage that would otherwise have been caused by the pilocarpine and MK-801, and the formation of vacuoles in cingulate/retrosplenial neurons.

The observation that MK-801 potentiates the convulsant effects of pilocarpine adds further evidence that a linking mechanism connects the excitotoxic processes that involve cholinergic receptors and NMDA receptors. The discovery that a cholinergic antagonist can block the convulsion potentiating effects of MK-801 further confirms that link, and indicates that by combining an anti-cholinergic agent with an NMDA antagonist such as MK-801, it is possible to utilize the anti-convulsive properties of both agents while eliminating the convulsion potentiating effects of the NMDA antagonist.

Thus, there has been disclosed a class of pharmacological agents which can function safely and effectively in accomplishing beneficial results which were not previously available. This invention therefore satisfies all of the objectives set forth herein. Although this invention has been described with respect to specific embodiments, the details of these embodiments are not to be construed as limitations. Various equivalents and modifications may be made without departing from the spirit and scope of this invention, which is limited only by the claims which follow.

REFERENCES

Adelman, G. (ed.), Encyclopedia of Neurosciences (Birkhauser, Boston, 1987)

Anis, N. A. et al, "The Dissociative Anaesthetics, Ketamine and Phencyclidine, Selectively Reduce Excitation of Central Mammalian Neurons by N-Methyl-Asparate", Br J Pharmacol 79:565 (1983)

Berry, S. D., et al, "Stereoselective Effects of Two Phencyclidine Derivatives on N-Methylaspartate Excitation of Spinal Neurones in the Cat and Rat", Eur J Pharm 96:261 (1983)

Boast, C. A., "Neuroprotection after brain ischemia: role of competitive NMDA antagonists," Neurology and Neurobiology 46:691–698 (1988)

Braitman, D. J., et al, "MK-801 protects against seizures and brain damage induced by the cholinesterase inhibitor soman," Neurosci. Abstr. 14:240 (1988)

Burke, R. E., "The relative selectivity of anticholinergic drugs for the M1 and M2 muscarinic receptor subtypes," Movement Disorders 1:135–144 (1986)

Clifford, D. B., et al, "The functional anatomy and pathology of lithium-pilocarpine and high-dose pilocarpine seizures," Neurosci. 23:953–968 (1987)

Clifford, D. B., et al, "Ketamine and MK-801 prevent degeneration of thalamic neurons induced by focal cortical seizures," Exp. Neurology 105:272–279 (1989).

Das, M., et al, Toxicol. Appl. Pharmacol. 39(1): 149–152 (1977)

Fleischhacker, W. W., et al, J. Affective Disorder 12(2): 153–157 (1987)

Freedman, S. B., et al, "Muscarinic M1, M2 receptor binding; Relationship with functional efficacy," Eur. J. Pharmacol 156:133–142 (1988)

Fuller, T. A. and Olney, J. W., "Only certain anti-convulsants protect against kainic acid neurotoxocity," Neurobiol. Toxicol. and Teratol. 3:355–361 (1981)

Goldman, M. E., et al, "Differentiation of [$^3$H]Phencyclidine and (+)-[$^3$H]SKF-10,047 Binding Sites in Rat Cerebral Cortex," FEBS Lett. 170:333–336 (1985)

Goodman, L. S. and Gilman, A., The Pharmacological Basis of Therapeutics (5th ed., Macmillan, N.Y., 1975)

Herrling, P. L., et al, "NMDA antagonistic properties of the enantiomers of CPP and CPP-ene," Soc. Neurosci Abstr. 15:327 (1989)

Hitri, A., et al, Psychpharmacol. Bull. 23(1): 33–37 (1987)

Honchar, M. P., et al, "Systemic cholinergic agents induce seizures and brain damage in lithium-treated rats," Science 220:323–325 (1983)

Kemp, J. D., et al, "Non-competitive antagonists of excitatory amino acid receptors," Trends in Neurosci 10:294 (1987)

Labruyere, J., et al, "Phencyclidine and ketamine protect against seizure-related brain damage," Neurosci. Abstr. 12:344 (1986)

Labruyere, J., et al, "NMDA antagonists induce pathomorphological changes in cerebrocortical neurons," Neurosci. Abst. 15:761 (1989)

Langlais, P. J., et al, "Acute thiamine deficiency in the rat: Brain lesions, amino acid changes and MK-801 pretreatment," Neurosci. Abst. 14:774 (1988)

Lawrence, J. J., Fuller, T. A., and Olney, J. W., "MK-801 and PCP protect against ischemic neuronal degeneration in the gerbil hippocampus," Neurosci Abstr. 13:1079 (1987).

Lodge, D., et al, "Excitatory amino acids and phencyclidine-like drugs," in Hicks, T. P., et al (Eds), Excitatory Amino Acid Transmission (Alan R. Liss, New York, 1987)

Mann, N., et al, Arch. Pharm. (Weinheim, Ger.) 309(4): 320–325 (1976)

Maragos, W., et al, "High Correlation Between the Localization of [$^3$H]TCP Binding and NMDA Receptors," Eur. J. Pharmacol. 123:173–174 (1986)

McEvoy, J. P., et al, Psychopharmacol. Bull. 23(1): 30–32 (1987)

McLeod, C. G., et al, "Acute neuropathology in soman-poisoned rats," Neurotoxicology 5:53–58 (1984)

Olney, J. W., "Glutamate-induced neuronal necrosis in the infant mouse hypothalamus: an electron microscopic study," J. Neuropathol. Exp. Neurol. 30:75–90 (1971)

Olney, J. W., "Excitotoxins: an overview," in Excitotoxins, Fuxe, K., et al, Eds. (Macmillan, London) pp 82–96 (1983)

Olney, J. W., et al, "The Anti-Excitotoxic Effects of Certain Anesthetics, Analgesics and Sedative Hypnotics," Neuroscience Letters 68:29–34 (1986)

Olney, J. W., et al, "Anti-Parkinsonian agents are phencyclidine agonists and N-methyl aspartate antagonists," Eur. J. Pharmacol. 142:319–320 (1987)

Olney, J. W., et al, "MK-801 powerfully protects against N-methyl aspartate neurotoxicity," *Eur. J. Pharmacol* 141:357 361 (1987)

Olney, J. W., "Excitatory amino acids and neuropsychiatric disorders," *Biol. Psychiatry* 26:505–525 (1989)

Olney, J. W., et al, "MK-801 prevents hypobaric-ischemic neuronal degeneration in infant rat liver," *J. Neurosci* 9:1701 (1989)

Olney, J. W., et al, "Pathological changes induced in cerebrocortical neurons by phencyclidine and related drugs." *Science* 244:1360–1362 (1989)

*Physicians Desk Reference,* 40th Edition (Medical Economics Co., 1986)

Price, M. T., et al, "Procyclidine protects against soman neurotoxicity, even when administered after onset of convulsions," *Neurosci Abst* 15:1349 (1989)

Quilliam, M. A. and Wright, J. L. C., "The amnesic shellfish poisoning mystery," *Analytical Chemistry* 61:1053–1059 (1989)

Quirion, R., "Phencyclidine (Angel Dust)/Sigma 'Opiate' Receptor: Visualization by Tritium-Sensitive Film," *Proc. Nat'l. Acad. Sci. U.S.A.* 78:5881 (1981)

Rothman, S. M., and Olney, J. W., "Glutamate and the Pathophysiology of Hypoxia-Ischemic Brain Damage," *Annals of Neurology* 19(2): 105–111 (1986)

Schroeder, C., et al, *Antiviral Res. Suppl.* 1:95–99 (1985)

Snell, L. D., et al, "Antagonism of NMDA-Induced Transmitter Release In The Rat Striatum By Phencyclidine-Like Drugs And Its Relationship To Turning Behavior," *J. Pharmacol. Exp. Ther.* 235:50–56 (1985)

Syvalahti, E. K. G., et al, *Pharmacol. Toxicol. (Copenhagen)* 60(1): 66–69 (1987)

Turski, W. A., et al, "Limbic seizures produced by pilocarpine in rats," *Behav. Brain Research* 9:315–335 (1983)

Wong, E. H. F., et al, "The Anticonvulsant MK-801 Is A Potent N-Methyl-D-Aspartate Antagonist," *Proc. Nat'l Acad Sci U.S.A.* 83: pp. 7104–7108 (Sept. 1986)

I claim:

1. A pharmacological composition comprising a mixture of an NMDA antagonist and an anti-cholinergic agent, both of which can penetrate blood-brain barriers, wherein the NMDA antagonist is present in a therapeutically effective quantity sufficient to reduce excitotoxic damage in the brain if administered to a mammal, and wherein the NMDA antagonist can cause neurotoxic side effects in the brain if administered without an accompanying anti-cholinergic agent, and wherein the anti-cholinergic agent is present in a second quantity that can reduce the neurotoxic side effects which would be caused by the NMDA antagonist if administered without the accompanying anti-cholinergic agent.

2. A pharmacological composition of claim 1, wherein the NMDA antagonist is selected from the group consisting of (+)-5-methyl-10,11-dihydro-5H-dibenzo[a,d]cyclohepten-5,10-imine maleate (common name MK-801), phencyclidine, ketamine, and tiletamine.

3. A pharmacological composition of claim 1, wherein the anti-cholinergic agent exerts a pharmaceutically antagonistic effect on cholinergic receptors of the M1 muscarinic type on the surfaces of neurons in the central nervous system.

4. A pharmacological composition of claim 2, wherein the anti-cholinergic agent exerts a pharmaceutically antagonistic effect on cholinergic receptors of the M1 muscarinic type on the surfaces of neurons in the central nervous system.

5. A pharmacological composition of claim 1, wherein the anti-cholinergic agent is selected from the group consisting of scopolamine, atropine, benztropine, benactyzine, biperiden, procyclidine, trihexyphenidyl, and diphenhydramine, and pharmaceutically acceptable salts thereof.

6. A pharmacological composition of claim 2, wherein the anti-cholinergic agent is selected from the group consisting of scopolamine, atropine, benztropine, benactyzine, biperiden, procyclidine, trihexyphenidyl, and diphenhydramine, and pharmaceutically acceptable salts thereof.

7. A pharmacological composition of claim 3, wherein the anti-cholinergic agent is selected from the group consisting of scopolamine, atropine, benztropine, benactyzine, biperiden, procyclidine, trihexyphenidyl, and diphenhydramine, and pharmaceutically acceptable salts thereof.

* * * * *